US007030253B2

(12) United States Patent
Gibson et al.

(10) Patent No.: US 7,030,253 B2
(45) Date of Patent: Apr. 18, 2006

(54) PROCESS FOR PREPARING 4-ALKYL- OR 4-ARYL-OXYCARBONYL PACLITAXEL ANALOGS AND NOVEL INTERMEDIATES

(75) Inventors: Frank S. Gibson, Pennington, NJ (US); Joydeep Kant, Cherry Hill, NJ (US); Rajendra P. Deshpande, Hillsborough, NJ (US); Karen L. TenHuisen, Randolph, NJ (US); Jing Liang, Princeton, NJ (US); Jun Li, Langhorne, PA (US); Susan D. Boettger, Fayetteville, NY (US); Edward J. Gublo, Liverpool, NY (US); Ulhas P. Dhokte, Jamesville, NY (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/909,899

(22) Filed: Aug. 2, 2004

(65) Prior Publication Data

US 2005/0054863 A1 Mar. 10, 2005

Related U.S. Application Data

(60) Provisional application No. 60/493,382, filed on Aug. 7, 2003.

(51) Int. Cl.
*C07D 305/14* (2006.01)
*C07F 7/18* (2006.01)

(52) U.S. Cl. .................................... 549/510; 549/214
(58) Field of Classification Search ................ 549/510, 549/214

See application file for complete search history.

(56) References Cited

U.S. PATENT DOCUMENTS

| 5,175,315 A | 12/1992 | Holton |
| 5,227,400 A | 7/1993 | Holton et al. |
| 5,229,526 A | 7/1993 | Holton |
| 6,020,507 A | 2/2000 | Gibson |
| 6,476,242 B1 | 11/2002 | Kingston et al. |
| 6,515,151 B1 | 2/2003 | Poss et al. |

OTHER PUBLICATIONS

Greene, T. W. et al., Protective Groups in Organic Synthesis, Second Edition, John Wiley & Sons, Inc., publ., pp. ix-x (table of contents) (1991).

*Primary Examiner*—Bernard Dentz
(74) *Attorney, Agent, or Firm*—Burton Rodney

(57) ABSTRACT

A process is provided for preparing 4-alkyl- or 4-aryl-oxycarbonyl paclitaxel analogs which includes the steps of converting paclitaxel into a C-7 acylprotected paclitaxel employing an electrophilic protecting group, such as benzoyloxycarbonyl, and converting the C-7 protected analog into the 4-alkyloxycarbonyl or 4-aryloxycarbonyl paclitaxel analog. Novel intermediates produced in the process are also provided.

16 Claims, No Drawings

PROCESS FOR PREPARING 4-ALKYL- OR 4-ARYL-OXYCARBONYL PACLITAXEL ANALOGS AND NOVEL INTERMEDIATES

This application claims a benefit of priority from U.S. Provisional Application No. 60/493,382 filed Aug. 7, 2003, the entire disclosure of which is herein incorporated by reference.

The present invention relates to a process for preparing 4-alkyloxycarbonyl or 4-aryloxycarbonyl paclitaxel analogs starting with paclitaxel and employing an electrophilic protecting agent such as benzyloxycarbonyl as a C-7 protecting group, and to novel intermediates produced therein.

FIELD OF THE INVENTION

Background of the Invention

Paclitaxel is a highly effective taxane anti-tumor agent currently marketed under the trademark Taxol® (Bristol-Myers Squibb Company) and having the structure

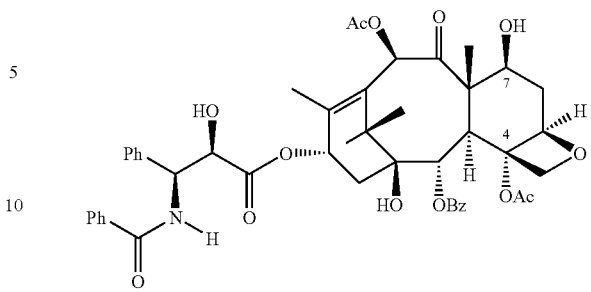

where Ph is phenyl, Ac is acetyl and Bz is benzoyl. Naturally occurring taxanes such as taxol may be found in plant materials, and have been isolated therefrom. Such taxanes may, however, be present in plant materials in relatively small amounts so that, in the case of paclitaxel, for example, large numbers of the slow-growing yew trees forming a source for the compound may be required. The art has thus continued to search for synthetic, including semi-synthetic routes for the preparation of taxanes such as paclitaxel and analogs thereof, as well as routes for the preparation of intermediates used in the preparation of these compounds.

U.S. Pat. No. 6,476,242 to Kingston et al. discloses a method for preparing 2-aroyl-4-acyl paclitaxel analogs by the following reaction route.

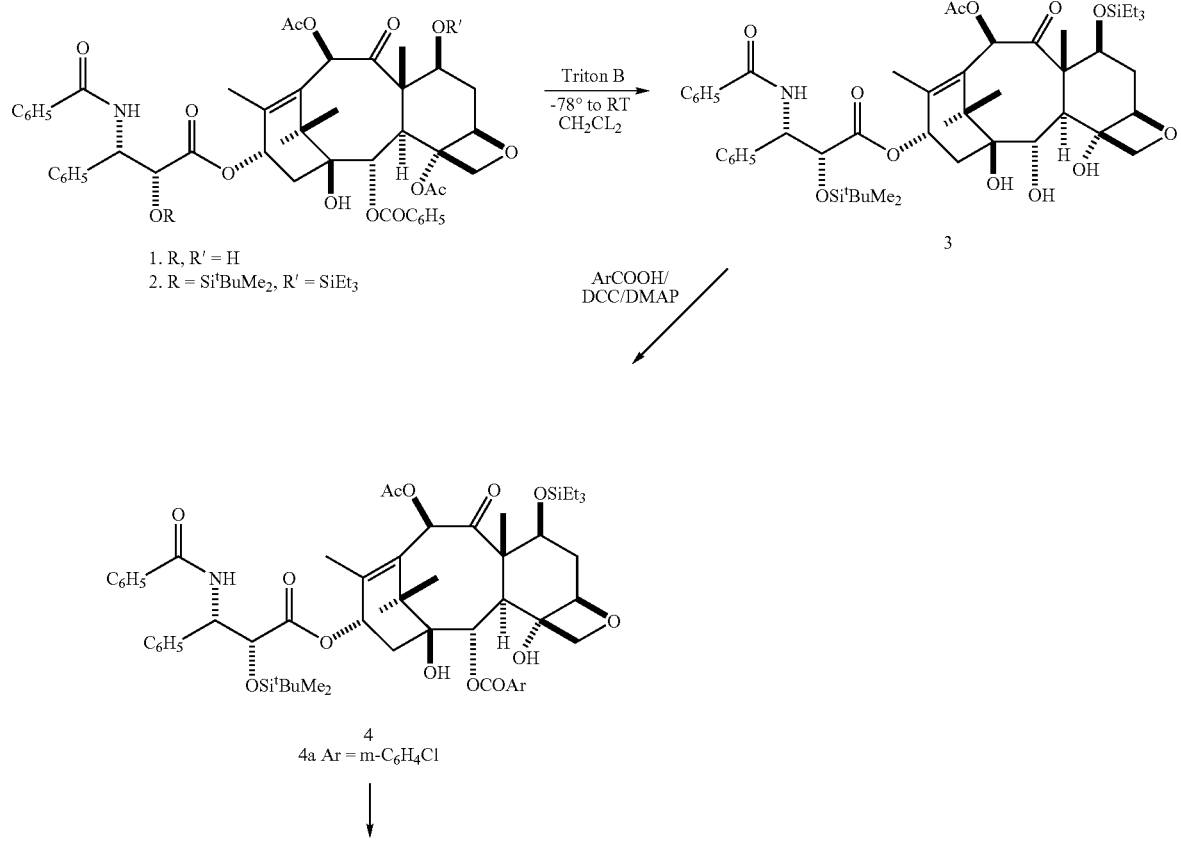

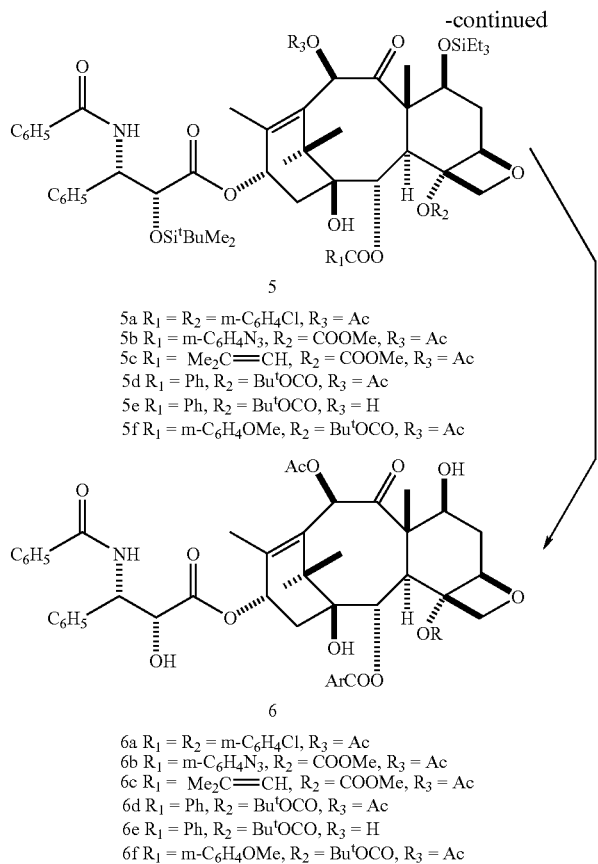

5a $R_1 = R_2 = m\text{-}C_6H_4Cl$, $R_3 = Ac$
5b $R_1 = m\text{-}C_6H_4N_3$, $R_2 = COOMe$, $R_3 = Ac$
5c $R_1 = Me_2C=CH$, $R_2 = COOMe$, $R_3 = Ac$
5d $R_1 = Ph$, $R_2 = Bu^tOCO$, $R_3 = Ac$
5e $R_1 = Ph$, $R_2 = Bu^tOCO$, $R_3 = H$
5f $R_1 = m\text{-}C_6H_4OMe$, $R_2 = Bu^tOCO$, $R_3 = Ac$ 6a $R_1 = R_2 = m\text{-}C_6H_4Cl$, $R_3 = Ac$
6b $R_1 = m\text{-}C_6H_4N_3$, $R_2 = COOMe$, $R_3 = Ac$
6c $R_1 = Me_2C=CH$, $R_2 = COOMe$, $R_3 = Ac$
6d $R_1 = Ph$, $R_2 = Bu^tOCO$, $R_3 = Ac$
6e $R_1 = Ph$, $R_2 = Bu^tOCO$, $R_3 = H$
6f $R_1 = m\text{-}C_6H_4OMe$, $R_2 = Bu^tOCO$, $R_3 = Ac$ A description of the above reaction sequence is set out in U.S. Pat. No. 6,476,242, Column 10, lines 7 to 26 and is reproduced below.

"In the first method, as illustrated in FIG. 1, paclitaxel (1) is converted to its 2'-t-butyldimethylsilyl-7-triethylsilyl derivative 2 by treatment in succession with t-butyldimethylsilyl chloride/imidazole and then with triethylsilyl chloride/pyridine. Treatment of 2 with Triton B under carefully defined conditions (−78° to −10°, $CH_2Cl_2$) gave the triol 3 (2-debenzoyl-4-deacetyl-2'-t-butyldimethylsilyl-7-triethylsilylpaclitaxel) as a key intermediate.

Treatment of the triol 3 with a desired substituted benzoic acid, such as m-methoxybenzoic acid, in the presence of DCC and DMAP, yielded the 2-acyl derivative 4. If the conditions are adjusted appropriately, the diacyl derivative 5, where R=Ar, can be prepared in good yield. However, treatment of 4 with excess carboxylic acid in the presence of DCC and DMAP yields the diacyl derivative 5 in modest yield, where Ar and R are independently selectable depending on the carboxylic acids used in the two acylation steps.

Deprotection of 5 under standard conditions (dilute HCl or HF/pyridine) yielded the diacyl paclitaxel analog 6."

U.S. application Ser. No. 09/592,879 now U.S. Pat. No 6,515,151 discloses a method for preparing sidechain-bearing taxanes which includes the following steps:

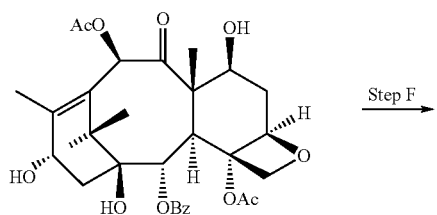

baccatin III

-continued

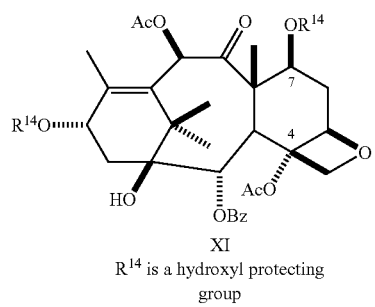

XI
R$^{14}$ is a hydroxyl protecting group

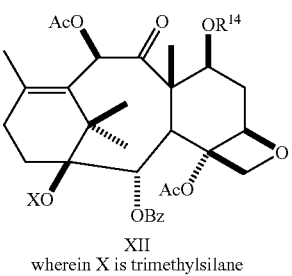

XII
wherein X is trimethylsilane or dimethylsilane

Step H

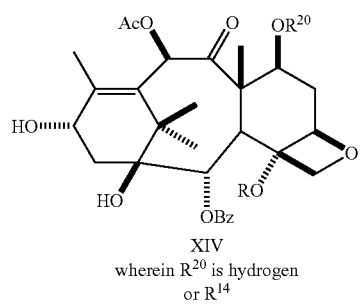

XIV
wherein R$^{20}$ is hydrogen or R$^{14}$

← Step I

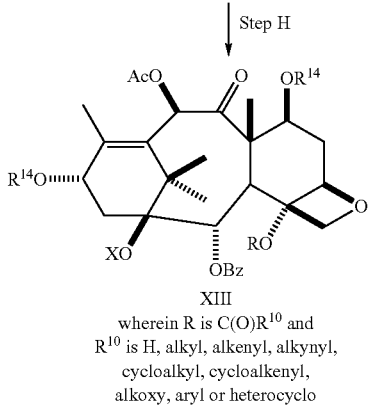

XIII
wherein R is C(O)R$^{10}$ and R$^{10}$ is H, alkyl, alkenyl, alkynyl, cycloalkyl, cycloalkenyl, alkoxy, aryl or heterocyclo A description of the above scheme is set out on pages 24 to 26 of application Ser. No. 09/592,879 and is reproduced below.

"Step F

Baccatin III is protected at the C-7 and C-13 sites by reaction with a suitable agent, such as, a halotrialkylsilane e.g. trimethyl or triethyl, 2,2,2-trichloroethyl chloroformate or carbobenzyloxy. Any inert organic solvent wherein Baccatin III is soluble may be utilized, such as, THF, DMF, MeCl$_2$ and dioxane. The reaction is carried out in the presence of a tertiary amine base, such as, pyridine or imidazole. The reaction temperature can vary from −30° C. to room temperature with C-7 substitution occurring preferably at −30° C. to 0° C. and C-13 at 0° C. to room temperature. The protecting group reactant concentration is preferably in molar excess (1–10) to effect both C-7 and C-13 substitution.

Step G

The intermediate XI is thereafter protected at the C-1 hydroxy by reaction with a trimethylsilane or preferably a dimethylsilane e.g. chlorotrimethylsilane or preferably chlorodimethylsilane in, for example, DMF, THF, dioxane or various ethers. As in step F the reaction is preferably carried out in the presence of a tertiary amine base, such as imidazole or pyridine. The temperature can range from −30° C. to room temperature with about 0° C. as preferred.

Step H (A) Intermediate XII is thereafter reduced at C-4 to hydroxy by reaction with a suitable reducing agent such as Red-Al or lithium aluminum hydride. The reducing agent is usually present in molar excess (1–5 equivalents). The reaction solvent can be THF, dioxane or various suitable ethers and the reaction temperature can range from −30° C. to 0° C. with about 0° C. as preferred.

(B) Intermediate XIII of (A) wherein C-4 is hydroxy is converted to the appropriate C-4 substituent by reaction with the appropriate acyl chloride acid anhydride or mixed anhydride e.g. acryloyl chloride, benzoyl chloride, cycloalkylcarbonyl chloride, alkyl chloroformate, in the presence of an alkali metal (Li, Na or K) anion of a secondary amine base. The reaction solvents include THF, dioxane, etc. The temperature range can be from −30° C. to room temperature with about 0° C. as preferred.

Step I (A) The intermediate XIII of step H (B) is thereafter deprotected by reaction with pyridinium fluoride (aqueous hydrogen fluoride in pyridine) in acetonitrile followed by tetrabutylammonium fluoride in THF or cesium fluoride in THF. Thereafter the mixture is diluted in an alcohol, washed with mild organic or inorganic acid and isolated.

(B) Thereafter the C-7 hydroxy protecting group may be introduced in XIV as in Step F following reaction parameters favoring C-7 substitution above.

Subsequently, the appropriate side chain may be introduced at C-13 following the novel process disclosed herein or alternatively via Holton methodology as disclosed in U.S. Pat. Nos. 5,227,400, 5,175,315 and 5,229,526 which are herein incorporated by reference."

The C-7 protecting group at C-7 site on the baccatin III employed is benzoyloxycarbonyl (Cbz) or t-butoxycarbonyl (BOC). Other electrophiles disclosed include those of the general formula

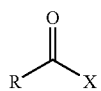

wherein R is alkyl, aryl, R'O—, or R'$_2$N—, RS, and X is halogen, imadozoyl, benztriazole, N-(benzyloxycarboxyloxy) succinimide, OR', or —OOCOR' and wherein R' is alkyl or alkenyl having 1–6 carbons atoms, benzyl, phenyl, trichloroethyl, trifluoroethyl, 2-trimethylsilylethyl or triisopropylsilyl.

Research is ongoing directed to the discovery and development of the next generation of novel taxane anti-tumor compounds, including analogs and derivatives of paclitaxel. One such derivative of paclitaxel of interest is the C-4 methyl carbonate analog of paclitaxel which has the structure

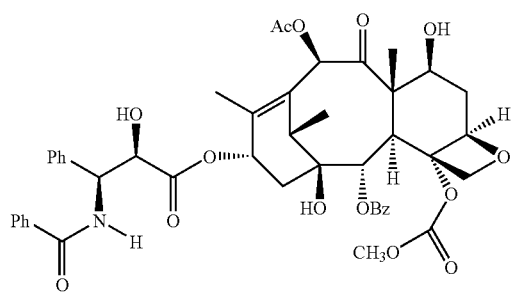

(hereinafter the C-4 methyl carbonate analog) and is disclosed in pending U.S. application Ser. No. 09/592,879 filed Jun. 13, 2000 now U.S. Pat. No. 6,515,151.

Attempts have been made to synthesize the C-4 methyl carbonate analog for paclitaxel. These generally have required long tedious routes, hazardous reagents, laborious purifications and poor overall yields. All such synthesis have involved protecting the C-7 hydroxyl of paclitaxel with a diisopropyl(methoxy)silyl group.

Early attempts to directly convert the C-4 acetate of paclitaxel to the methyl carbonate by hydrolysis/alcoholysis followed by methoxycarbonylation were unsuccessful due to lack of selectivity of hydrolysis and racemization at the C-7 alcohol. The C-7 alcohol is sensitive to epimerization due to its being β to the C-10 ketone. Under basic conditions, a retro aldol mechanism is active which gives an open ring aldehyde in equilibrium with the closed ring 2° alcohol. Upon closing, both the α and β alcohols are formed.

U.S. Pat. No. 6,020,507 to Gibson discloses a method for making paclitaxel from baccatin III using a strong base and an electrophile. The Gibson method involves protecting the 7-hydroxyl of the paclitaxel precursor baccatin In to provide 7-O-protected baccatin III using a strong base such as lithium tert-butoxide (or other strong base such as lithium hexamethyldisilazane (LiHMDS), potassium hexamethyldisilazane (KHMDS) or sodium hexamethyldisilazane (NAHMDS) in DMF (or similar solvent such as DMAC, NMPO, DMEU and DMPU), and various electrophiles followed by the coupling of a paclitaxel sidechain at the C-13 position and subsequent deprotection of the C-7 and replacement of the protecting group with a hydrogen.

DESCRIPTION OF THE INVENTION

In accordance with the present invention, a process is provided for forming 4-alkyloxycarbonyl or 4-aryloxycarbonyl paclitaxel analogs having the structure

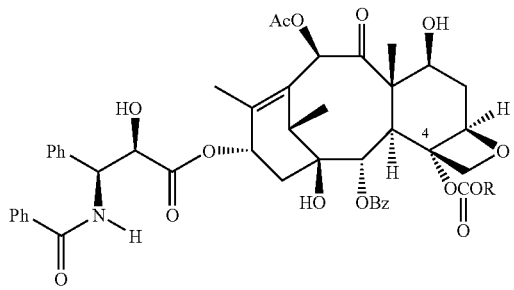

where R is $C_1$–$C_7$ alkyl or aryl, which process eliminates use of costly, dangerous and environmental unfriendly reagents while minimizing unit operations and intermediate isolations. This is especially critical for producing cytotoxic agents where exposure to them and their precursors can be a significant risk to production personnel.

The process of the invention described herein involves the production of novel C-7-O-protected paclitaxel, such as C-7-OCbz- or C-7-O-BOC paclitaxel, the coupling of an alkyloxycarbonyl or aryloxycarbonyl sidechain at C-4, and the subsequent deprotection of C-7 to form the 4-alkyloxycarbonyl or 4-aryloxycarbonyl analog of paclitaxel.

In accordance with the present invention, a process is provided for preparing a 4-alkyloxycarbonyl or 4-aryloxycarbonyl paclitaxel analog of the structure

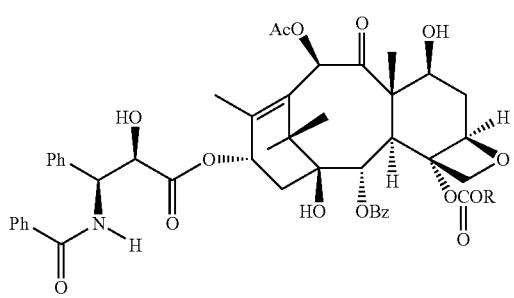

where R is $C_1$–$C_7$ alkyl or aryl, which process includes the step of converting paclitaxel into 7-0-acyl protected paclitaxel employing an electrophilic protecting agent, preferably benzoyloxycarbonyl chloride, and a strong base, preferably lithium t-butoxide.

The electrophilic protecting group includes benzyloxycarbonyl (Cbz), t-butoxycarbonyl (BOC), or may be provided by the electrophilic protecting agent of the general formula

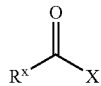

wherein $R^x$ is alkyl, aryl, R'O—, or R'$_2$N—, R'S, and X is halogen, imadozoyl, benzotriazole, N-(benzyloxycarboxyloxy) succinimide, OR', or —OOCOR' and wherein R' is alkyl or alkenyl having 1–6 carbons atoms, benzyl, phenyl, trichioroethyl, trifluoroethyl, 2-trimethylsilylethyl or triisopropylsilyl.

The preferred electrophilic protecting group is benzoyloxycarbonyl (Cbz).

In another aspect of the present invention, a process is provided for preparing a compound having the structure (9)

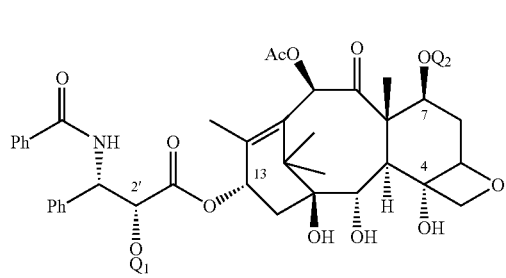

where $Q_1$ is tri $C_1$–$C_4$ alkylsilyl;

$Q_2$ is an electrophilic protecting group which is benzoyloxycarbonyl (Cbz), t-butoxycarbonyl (BOC), or may be provided by the electrophilic protecting agent of the general formula

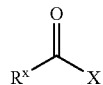

wherein $R^x$ is alkyl, aryl, R'O—, R'$_2$N—, or R'S, and X is halogen, imidazoyl, benzotriazole, N-(benzyloxycarboxyloxy) succinimide, OR', or —OOCOR' and wherein R' is alkyl or alkenyl having 1–6 carbons atoms, benzyl, phenyl, trichloroethyl, trifluoroethyl, 2-trimethylsilylethyl or triisopropylsilyl, which includes the steps of:

(a) subjecting paclitaxel having the structure (1)

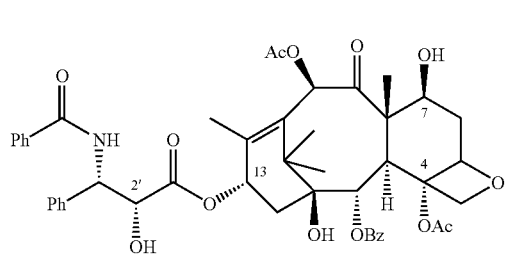

to silyl protection by treating paclitaxel with a tri-$C_1$–$C_4$ alkylsilyl chloride in the presence of a base and organic solvent to form the protected compound (7) of the structure (7)

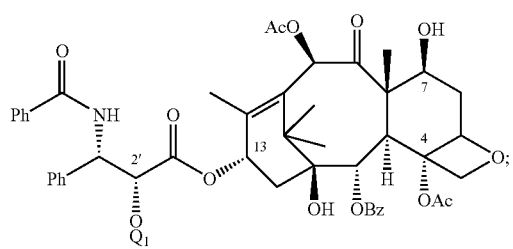

(b) treating compound (7) with a $Q_2$-protecting agent in the presence of a base and an organic solvent to form the $Q_2$-protected compound (8) of the structure (8)

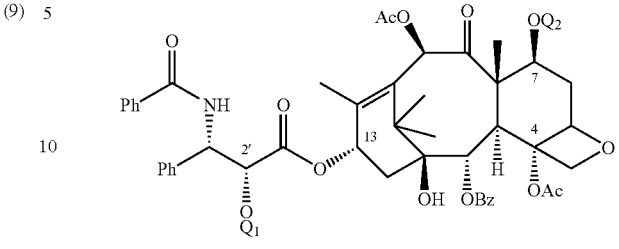

and (c) deprotecting compound (8) by treating compound (8) with an ammonium compound of the structure (R)$_4$N$^+$X wherein R is $C_1$–$C_7$ alkyl or aryl, and X is —OCH$_3$ or a halogen, in the presence of dichloromethane to form compound (9).

In a preferred embodiment, $Q_1$ is tert-butyldimethylsilyl chloride; $Q_2$ is benzoyloxycarbonyl (Cbz).

It is preferred that, in step (a) the paclitaxel is treated with tert-butyldimethylsilyl chloride in the presence of imidazole and dimethylformamide;

in step (b) compound (7) is treated with CbzCl in the presence of Li t-butoxide and ethyl acetate; and in step (c) compound (8) is treated with benzyltrimethylammonium methoxide in the presence of dichloromethane at a temperature within the range from about –10° to about –20° C.

In another embodiment of the present invention, a process is provided for preparing a compound of the structure (2)

(2)

wherein R is $C_1$–$C_7$ alkyl or aryl, which includes the steps of:

(a) providing a Cbz protected compound of the structure (9)

(9)

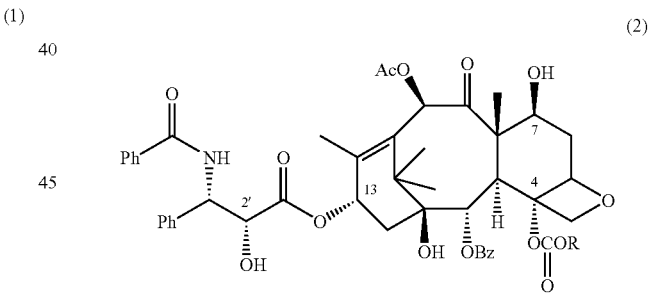

(b) treating compound (9) with a benzoyl (Bz) protecting agent in the presence of a base and an organic solvent to form the Bz protected compound (10)

(10)

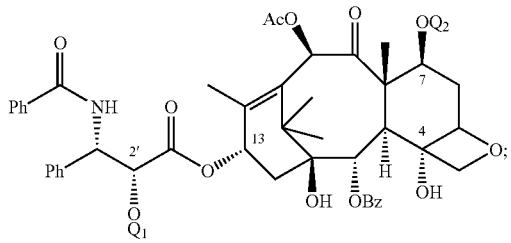

(c) subjecting compound (10) to carbonate formation by treating compound (10) with a haloformate of the structure ROOCX wherein X is Cl, Br, F or I, (ROOC)$_2$O, or R-pyrocarbonate, wherein R is $C_1$–$C_7$ alkyl or aryl, in the presence of an organic solvent, a base and a catalyst to form R-oxycarbonyl substituted compound (11) of the structure (11)

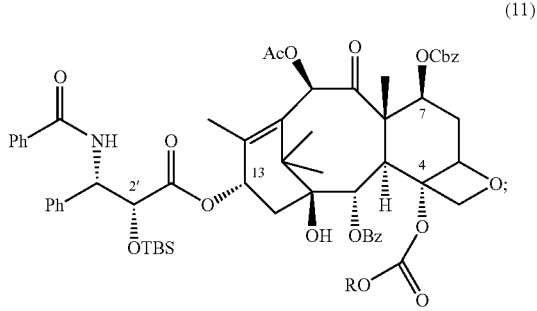

and (d) subjecting compound (11) to catalytic transfer-hydrogenation by treating compound (11) with a deprotecting agent in the presence of an organic acid, organic solvent, catalyst and formate compound such as ammonium formate, formic acid or sodium formate, or hydrogen, to form the compound (2).

In a preferred embodiment, in step (b) the benzoyl protecting agent is benzoyl chloride, the base is Li t-butoxide, and the organic solvent is ethyl acetate;

in step (c) the base is Li t-butoxide, the haloformate is methyl chloroformate, the organic solvent is ethyl acetate and the catalyst is dimethyl formamide; and in step (d) the deprotecting agent is tetrabutylammonium fluoride, the acid is acetic acid, the organic solvent is ethyl acetate, the catalyst is Pd/C and the formate compound is ammonium formate.

Still further in accordance with the present invention, a process is provided for preparing a taxane having the structure (2)

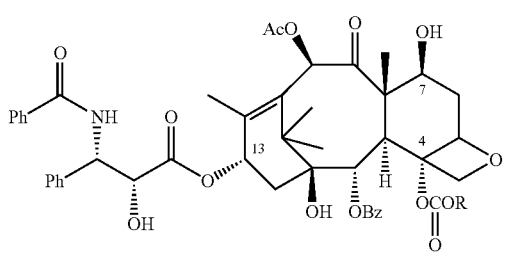

wherein R is $C_1$–$C_7$ alkyl or aryl which includes the following steps:

(a) subjecting paclitaxel having the structure (1)

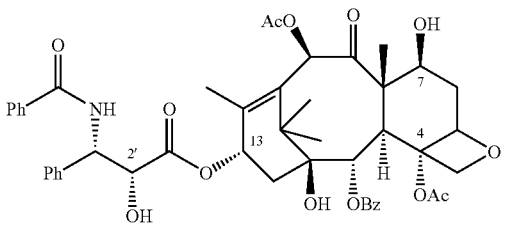

to silyl protection by treating paclitaxel with a tri-$C_1$–$C_4$-alkylsilyl chloride in the presence of a base and organic solvent to form the protected compound (7) of the structure (7)

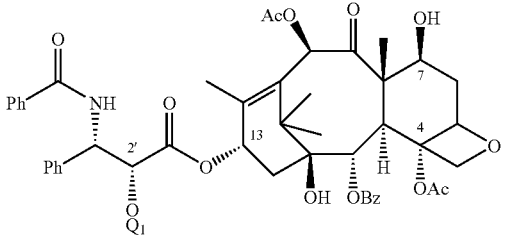

wherein $Q_1$ is a tri $C_1$–$C_4$ alkylsilyl group;

(b) treating compound (7) with an electrophilic ($Q_2$) protecting agent, as defined above, in the presence of a base and an organic solvent to form the 7-protected compound (8) of the structure (8)

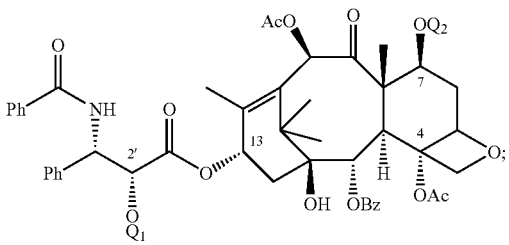

(c) deprotecting compound (8) by treating compound (8) with an ammonium compound of the structure (R)$_4$N$^+$X wherein R is $C_1$–$C_7$ alkyl or aryl and X is OCH$_3$ or a halogen, in the presence of dichloromethane to form compound (9);

(d) treating compound (9) with a benzoyl (Bz) protecting agent in the presence of a base and an organic solvent to form the Bz protected compound (10);

(e) subjecting compound (10) to carbonate formation by treating compound (10) with a haloformate of the structure ROOCX wherein X is Cl, Br, F or I, (ROOC)$_2$O, or R-pyrocarbonate, in the presence of an organic solvent, a base and a catalyst to form R-oxycarbonyl substituted compound (11) of the structure (11)

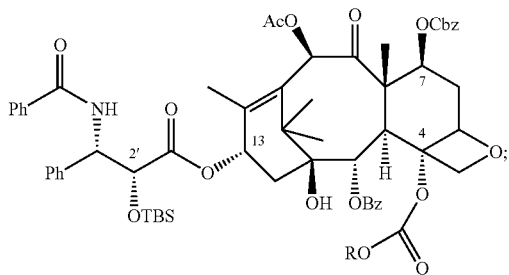

and (f) subjecting compound (11) to catalytic transfer-hydrogenation by treating compound (11) with a deprotecting agent in the presence of an acid, organic solvent, catalyst and formate compound or hydrogen, to form the compound (2).

The following novel paclitaxel intermediates are produced by the process of the invention (8)

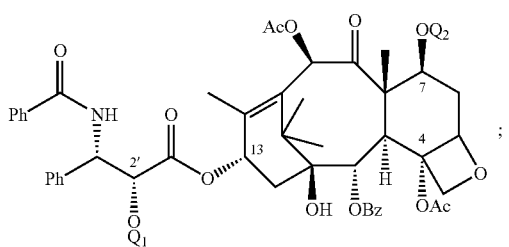

(9)

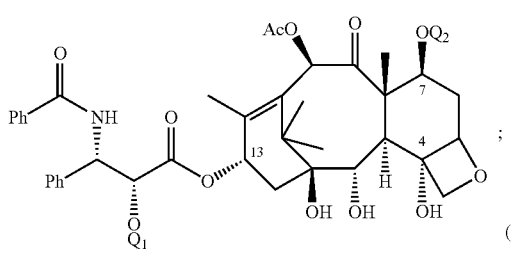

(10)

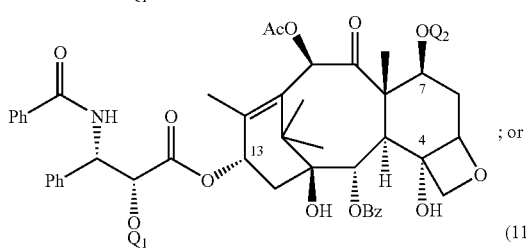

(11)

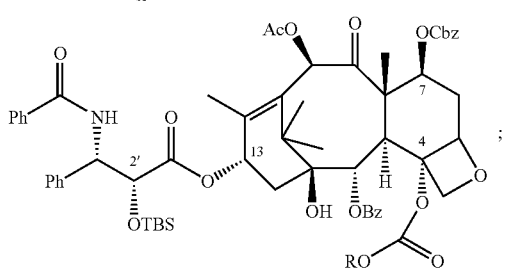

wherein $Q_1$ is a silyl protecting as defined herein, $Q_2$ is a C-7 protecting agent delivered by an electrophile as defined herein, and wherein R is $C_1$–$C_7$ alkyl or aryl.

Novel intermediates (8), (9), (10) and (11) include all stereoisomers thereof, either substantially free of other stereoisomers, or in admixture with other selected, or all other stereoisomers.

DETAILED DESCRIPTION OF THE INVENTION

The present invention is described further as follows.

The terms "alkyl" or "alk", as used herein alone or as part of another group, denote optionally substituted, straight and branched chain saturated hydrocarbon groups, preferably having 1 to 10 carbons in the normal chain, most preferably lower alkyl groups. Exemplary alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Alkyl may include 1 to 4 substituents which include one or more of the following groups: halo, alkoxy, alkylthio, alkenyl, alkynyl, aryl (e.g., to form a benzyl group), cycloalkyl, cycloalkenyl, hydroxy or protected hydroxy, carboxyl (—COOH), alkyloxycarbonyl, alkylcarbonyloxy, alkylcarbonyl, carbamoyl (NH$_2$—CO—), substituted carbamoyl (($R^5$)($R^6$)N—CO— where $R^5$ or $R^6$ are the same or different and are independently selected from $C_1$–$C_4$ alkyl or aryl except that at least one of $R^5$ or $R^6$ is not hydrogen), amino (—NH$_2$), heterocyclo, mono- or dialkylamino. or thiol (—SH).

The terms "lower alk" or "lower alkyl" as used herein, denote such optionally substituted groups as described above for alkyl having 1 to 4 carbon atoms in the normal chain.

The terms "alkoxy" or "alkylthio" denote an alkyl group as described above bonded through an oxygen linkage (—O—) or a sulfur linkage (—S—), respectively. The term "alkyloxycarbonyl", as used herein, denotes an alkoxy group bonded through a carbonyl group. The term "alkylcarbonyl", as used herein, denotes an alkyl group bonded through a carbonyl group. The term "alkylcarbonyloxy", as used herein, denotes an alkyl group bonded through a carbonyl group which is, in turn, bonded through an oxygen linkage. The terms "monoalkylamino" or "dialkylamino" denote an amino group substituted by one or two alkyl groups as described above, respectively.

The term "alkenyl", as used herein alone or as part of another group, denotes optionally substituted, straight and branched chain hydrocarbon groups containing at least one carbon to carbon double bond in the chain, and preferably having 2 to 10 carbons in the normal chain. Exemplary unsubstituted such groups include ethenyl, propenyl, isobutenyl, butenyl, pentenyl, hexenyl, heptenyl, octenyl, nonenyl, decenyl, and the like. Exemplary substituents may include one to four of the following groups: halo, alkoxy, alkylthio, alkyl, alkynyl, aryl, cycloalkyl, cycloalkenyl, hydroxy or protected hydroxy, carboxyl (—COOH), alkyloxycarbonyl, alkylcarbonyloxy, alkylcarbonyl, carbamoyl (NH$_2$—CO—), substituted carbamoyl (($R^5$)($R^6$)N—CO— where $R^5$ or $R^6$ are as defined above, except that at least one of $R^5$ or $R^6$ is not hydrogen), amino (—NH$_2$), heterocyclo, mono- or dialkylamino, or thiol (—SH).

The term "alkynyl", as used herein alone or as part of another group, denotes optionally substituted, straight and branched chain hydrocarbon groups containing at least one carbon to carbon triple bond in the chain, and preferably having 2 to 10 carbons in the normal chain. Exemplary unsubstituted such groups include ethynyl, propynyl, butynyl, pentynyl, hexynyl, heptynyl, octynyl, nonynyl, decynyl, and the like. Exemplary substituents may include one to four of the following groups: halo, alkoxy, alkylthio, alkyl, alkenyl, aryl, cycloalkyl, cycloalkenyl, hydroxy or protected hydroxy, carboxyl (—COOH), alkyloxycarbonyl, alkylcarbonyloxy, alkylcarbonyl, carbamoyl ($NH_2$—CO—), substituted carbamoyl (($R^5$)($R^6$)N—CO— where $R^5$ or $R^6$ are as defined above, except that at least one of $R^5$ or $R^6$ is not hydrogen), amino (—$NH_2$, heterocyclo, mono- or dialkylamino, or thiol (—SH).

The term "cycloalkyl", as used herein alone or as part of another group, denotes optionally substituted, saturated cyclic hydrocarbon ring systems, preferably containing 1 to 3 rings and 3 to 7 carbons per ring. Exemplary unsubstituted such groups include cyclopropyl, cyclobutyl, cyclopentyl, cyclohexyl, cycloheptyl, cyclooctyl, cyclodecyl, cyclododecyl, and adamantyl. Exemplary substituents include one to four alkyl groups as described above, or one to four groups described above as alkyl substituents.

The term "cycloalkenyl", as used herein alone or as part of another group, denotes such optionally substituted groups as described above for cycloalkyl, further containing at least one carbon to carbon double bond forming a partially unsaturated ring.

The terms "ar" or "aryl", as used herein alone or as part of another group, denote optionally substituted, homocyclic aromatic groups, preferably containing 1 or 2 rings and 6 to 12 ring carbons. Exemplary unsubstituted such groups include phenyl, biphenyl, and naphthyl. Exemplary substituents include one to four, preferably three or fewer, nitro groups, alkyl groups as described above or groups described above as alkyl substituents.

The terms "heterocyclo" or "heterocyclic", as used herein alone or as part of another group, denote optionally substituted fully saturated or unsaturated, aromatic or non-aromatic cyclic groups having at least one heteroatom in at least one ring, preferably monocyclic or bicyclic groups having 5 or 6 atoms in each ring. The heterocyclo group may, for example, have 1 or 2 oxygen atoms, 1 or 2 sulfur atoms, and/or 1 to 4 nitrogen atoms in the ring. Each heterocyclo group may be bonded through any carbon or heteroatom of the ring system. Exemplary heterocyclo groups include the following: thienyl, furyl, pyrrolyl, pyridyl, imidazolyl, pyrrolidinyl, piperidinyl, azepinyl, indolyl, isoindolyl, quinolinyl, isoquinolinyl, benzothiazolyl, benzoxazolyl, benzimidazolyl, benzoxadiazolyl, and benzofurazanyl. Exemplary substituents include one to four alkyl groups as described above or one or more groups described above as alkyl substituents. Also included are smaller heterocyclos, such as, epoxides and aziridines.

The terms "halogen", "halo", or "hal", as used herein alone or as part of another group, denote chlorine, bromine, fluorine, and iodine.

The term "taxane moiety", as used herein, denotes moieties containing the core structure:

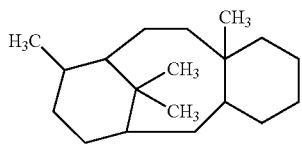

which core structure may be substituted and which may contain ethylenic unsaturation in the ring system thereof.

The term "taxane", as used herein, denotes compounds containing a taxane moiety as described above.

The term "hydroxy (or hydroxyl) protecting group", as used herein, denotes any group capable of protecting a free hydroxyl group which, subsequent to the reaction for which it is employed, may be removed without destroying the remainder of the molecule. Such groups, and the synthesis thereof, may be found in "Protective Groups in Organic Synthesis" by T. W. Greene, John Wiley and Sons, 1991, or Fieser & Fieser. Exemplary hydroxylprotecting groups include methoxymethyl, 1-ethoxyethyl, 1-methoxy-1-methylethyl, benzyloxymethyl, (β-trimethylsilylethoxy)methyl, tetrahydropyranyl, 2,2,2-trichloroethoxycarbonyl, t-butyl (diphenyl)silyl, trialkylsilyl, trichloromethoxycarbonyl, and 2,2,2-trichloroethoxymethyl.

The term "salt" includes acidic and/or basic salts formed with inorganic and/or organic acids and bases. Exemplary acidic salts include salts formed with mineral acids such as HCl, $H_2SO_4$, or $HNO_3$, or carboxylic acids such as trifluoroacetic acid or acetic acid. Exemplary basic salts include salts formed with amines such as triethylamine, diisopropylethylamine, or pyridine or amino acids such as arginine, or guanidine. Salts of hydroxyl groups, such as metal (e.g., alkali or alkaline earth metal) alkoxides, are also contemplated as "salts" herein. Metal alkoxide salts may, for example, be formed by contacting a hydroxyl group with a metallating agent.

Reference to a compound employed in or prepared by the methods of the present invention includes salts and hydrates thereof, unless otherwise indicated.

The following reaction scheme sets out the process of the invention. Although the reaction scheme may set out specific reagents, solvents, catalysts and the like and specific stereochemistry, all of which are preferred, it is to be understood that any of the reagents, solvents, catalysts set out herein in the description of the reaction scheme and all possible stereochemistry may be employed. It is preferred to employ a single stereoisomer, preferably the stereoisomers shown in the reaction schemes, although stereoisomeric mixtures may be employed as well.

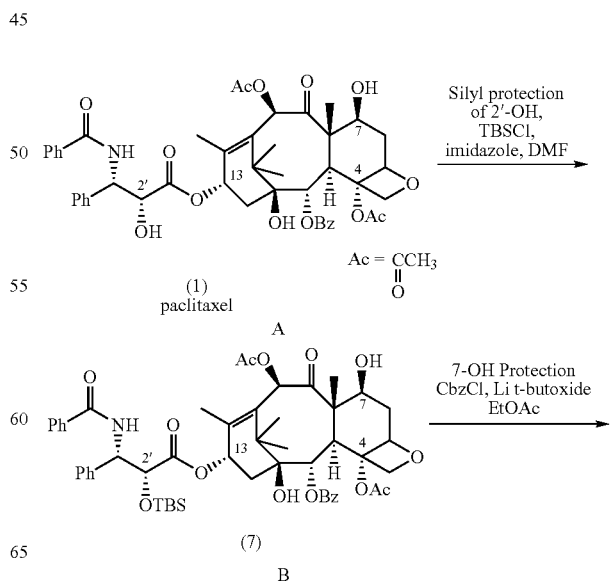

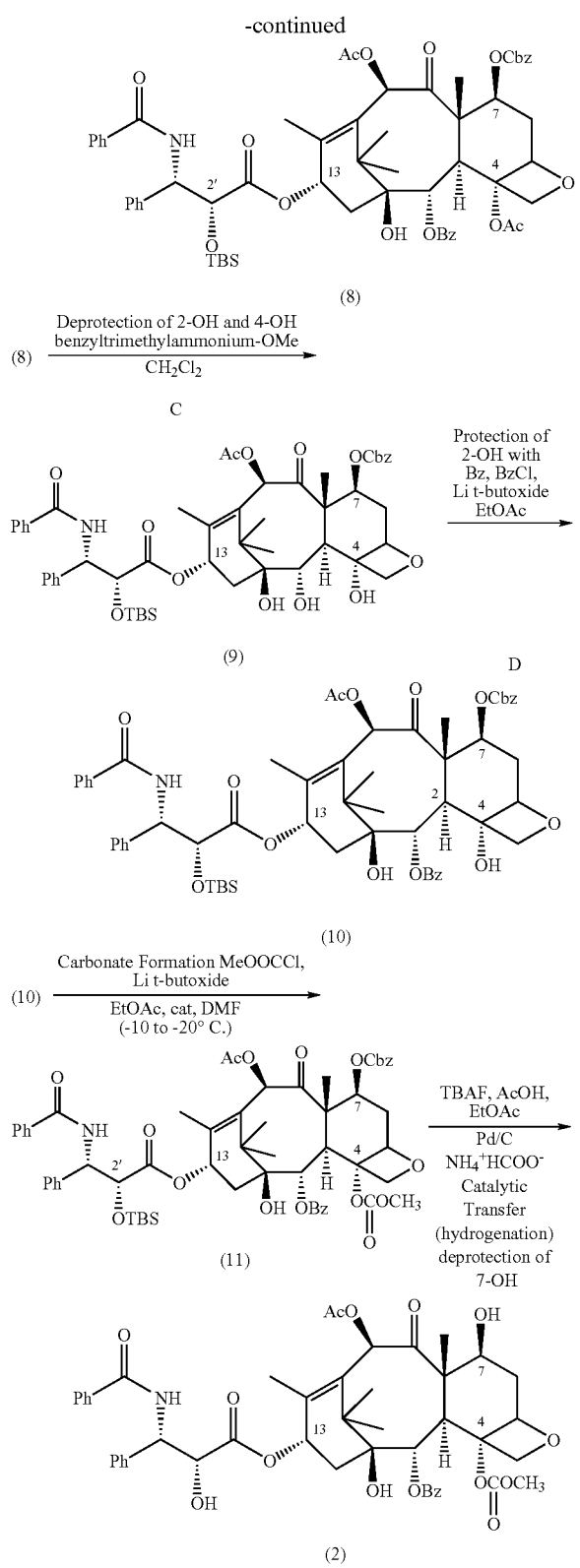

As seen in the above reaction scheme, paclitaxel (1) is made to undergo silyl protection of the 2'-OH wherein paclitaxel is treated with a tri $C_1$–$C_4$ alkylsilyl chloride, (which 3 alkyl groups may be the same or different), preferably tert-butyldimethylsilyl chloride (as shown) as well as triethylsilyl chloride or diisopropylmethoxy, in the presence of a base and organic solvent to give the desired 2'-silyl ether (7). The above reaction is carried out employing a molar ratio of trialkylsilyl chloride to paclitaxel (1) within the range from about 1.0:1 to about 4:1, preferably from about 1.5:1 to about 2.5:1, at a temperature within the range from about 0° C. to about 30° C., preferably from about 10° C. to 25° C. to about ° C.

The base which may be employed in forming 2'-silyl ether (7) is preferably imidiazole, although other bases such as tertiary-amines such as triethylamine or diisopropylethylamine, or pyridine may be employed as well.

The 2'-silylation step will be carried out in the presence of an organic solvent which is an ester or amide solvent such as dimethylformamide (DMF), N,N'-dimethylacetamide (DMAC), N,N'-dimethylpropyleneurea (DMPU), N,N'-dimethylethyleneurea (DMEU) or N-methyl-2-pyrrolidinone (NMPO). The 2'-silyl ether (7) is then subjected to 7-OH protection wherein the 2'-silyl ether (7) is reacted with one or more strong bases to provide a 7-O-anion suitable for reaction with an electrophile/protecting agent. The base will preferably be Li t-butoxide, although other bases having the structure $R^3OM$ where $R^3$ is $C_1$–$C_6$ alkyl and M is Li, Na or K may be employed as well as lithium hexamethyldisilazane (LiHMDS), sodium hexamethyldisilazane (NaHMDS), and potassium hexamethyldisilazane may be used as well.

Although both epimers of the C-7 anion will be present in solution, only the desired product is formed which is reacted with the electrophile, preferably benzyloxycarbonyl chloride (CbzCl), although other electrophiles such as CbzBr, CbzF and Cbz anhydride may be employed as well. Other non-silyl electrophiles include those of the general formula

wherein $R^x$ is alkyl, aryl, R'O—, $R'_2$N—, or R'S, and X is halogen; imidazoyl, benztriazole, N-(benzyloxycarboxyloxy) succinimide, OR', or —OOCOR' wherein R' is alkyl or alkenyl having 1–6 carbons atoms, benzyl, trichloroethyl or trifluoroethyl. The use of a non-silyl protecting agent such as the Cbz protecting agent to protect the 7-OH is indeed novel and unique.

The above reaction of 2'-silyl ether (7) is carried out in the presence of an organic solvent such as an ester or amide solvent, preferably ethyl acetate, although methyl acetate, butyl acetate, DMF, DMPU, DMEU and NMPO may be used as well.

In carrying out the formation of the 7-Cbz protected compound (8), the Cbz electrophile will be employed in a molar ratio to 2'-silyl ether (7) within the range from about 1.5:1 to about 4:1, preferably from about 2:1 to about 3:1, at a temperature within the range from about 0 to about 30° C., preferably from about 10 to about 25° C.

The C-4 acetate and the C-2 benzoate of compound (8) are removed to form compound (9) by treating (8) with an ammonium compound, preferably, benzyltrimethylammonium methoxide, in the presence of dichloromethane, at a temperature below about –10° C., and preferably within the range from about –10 to about –20° C. The ammonium compound is employed in a molar ratio to (8) within the range from about 25:1 to about 0.5:1, preferably from about 0.5:1 to about 1:1.

In carrying out the conversion of (8) to (9), compound (8) is treated with an ammonium compound of the structure (Rx)₄N⁺X where Rx is $C_1$–$C_7$ alkyl or aryl and X is $OCH_3$ or a halogen, such as benzyltrimethylammonium chloride, tetrabutylammonium chloride or benzyltrimethylammonium methoxide.

Before the C-4 sidechain can be added to the C-7 Cbz protected paclitaxel analog (9), the analog (9) must undergo protection of the 2-OH. The protection step is carried out by treating the reaction mixture containing analog (9) with an acid, preferably acetic acid to neutralize the reaction mixture. The dichloromethane in the neutralized reaction mixture is exchanged for ethyl acetate or other ester or amide organic solvent, and the resulting solution of 9 is treated with a strong base, preferably Li t-butoxide, and a benzoyl protecting agent, preferably benzoyl chloride, to form the 2-benzoyl (Bz) 7-hydroxy protected paclitaxel (10).

In carrying out the conversion of (9) to (10), the reaction will be conducted at a temperature within the range from about –10 to about 20° C., preferably from about 0 to about 10° C. The strong base employed is preferably Li t-butoxide but may be any of the strong bases set out hereinbefore with respect to the conversion of (7) to (8).

The ester or amine organic solvent employed will be any of the solvents employed in the conversion of (7) to (8), preferably ethyl acetate.

The benzoyl protecting agent will be employed in a molar ratio to compound (8) within the range from about 1:1 to about 1.3:1, preferably from about 1:1 to about 1.11. The benzoyl protecting agent will preferably be benzoyl chloride, although benzoyl bromide, benzoyl fluoride or benzoyl anhydride Bz₂O may be employed as well.

Installation of the required C-4 alkyl- or aryl-carbonate side chain, preferably C-4 methyl carbonate, is accomplished by treating paclitaxel analog (10) with a strong base, preferably Li t-butoxide, and a halo formate, preferably methylchloroformate in the presence of an ester or amine organic solvent and a catalytic amount of an amide solvent, preferably dimethylformamide, at a temperature below about –10° C., preferably within the range from about –10 to about –20° C.

In carrying out the conversion of (10) to (11), the C-4 alkyl- or aryl-carbonate substituted paclitaxel analog, the halo formate reactant will be employed in a molar ratio to (10) within the range from about 1 to about 2, preferably from about 1.1 to about 1.5.

The strong base employed in the conversion of (10) to (11) is preferably Li t-butoxide but any of the bases used in the conversion of (7) to (8) may be employed here as well.

The halo formate will have the structure

ROOCX or (ROOC)₂O or R pyrocarbonate, wherein R is $C_1$–$C_7$ alkyl or aryl and $X_2$ is Cl, Br, F or I, and preferably will be methyl chloroformate. Another example of suitable alkyl or aryl formates is methylpyrocarbonate.

The ester or amine organic solvent suitable for use in the formation of (11) will preferably be ethyl acetate although any of the organic solvents employed in the formation of (8) may be employed as well.

It is preferred that the reaction to form (11) include catalytic amounts of an organic solvent, preferably dimethylformamide. Other suitable catalysts include N,N'-dimethylpropyleneurea, N,N'-dimethylethyleneurea, N,N-dimethylacetamide, and N-methyl-2-pyrrolidinone. The catalyst will be employed in an amount within the range from about 5 to about 20% by volume and preferably from about 5 to about 10% by volume, based on the volume of the reaction mixture.

The 4-alkyl- or aryl-carbonate substituted paclitaxel analog (11) is then made to undergo deprotection to remove the C-7 protecting group (for example Cbz) and the 2'-silyl protecting group. This may be accomplished separately or together in one reaction vessel. Thus, compound (11) may be subjected to catalytic transfer (hydrogenation) by treating (11) with a deprotecting agent which preferably is a fluoride-containing deprotecting agent such as tetrabutylammonium fluoride (TBAF), hydrogen fluoride, triethylamine.3HF or M"F where M" is an alkali methyl such as Na, Li or K with tetrabutylammonium fluoride being preferred.

The reaction to form compound (2) will be carried in the presence of an organic acid for example a $C_1$–$C_4$ alkyl COOH, such as acetic acid, propionic acid, butyric acid, or benzoic acid, with acetic acid being preferred; and a reducing agent such as a formate like ammonium formate, sodium formate, formic acid or $H_2$, in the presence of a hydrogenation catalyst such as palladium, platinum or ruthenium with palladium on charcoal being preferred.

The organic solvent employed in the above reaction will preferably be ethyl acetate but may be any of the ester or amine solvents employed in forming compound (8).

In carrying out the reaction to form compound (2), silyl deprotecting agent will be employed in a molar ratio to (1) within the range from about 1:1 to about 2:1, preferably from about 1.1:1 to about 1.3:1; the acid will be employed in a molar ratio to (11) within the range from about 1:1 to about 2:1, preferably from about 1.1:1 to about 1.3:1. The Cbz deprotecting agent catalyst will be enployed in a molar ratio to (11) within the range from about 0.01:1 to about 0.1:1, preferably from about 0.01:1 to about 0.05:1. The formate reagent will be employed in a molar ratio to (11) within the range from about 4:1 to about 8:1, preferably from about 5:1 to about 7:1.

The reaction to remove the silyl group will be carried out at a temperature within the range from about 5° to about 50° C., preferably from about 15 to about 30° C. The reaction to remove the Cbz group will be carried out at a temperature within the range from about 25° C. to about 75° C., preferably from about 40 to about 60° C.

It will be understood that the various intermediates and products formed in carrying out the processes of the invention may be isolated and purified, if desired, employing conventional techniques such as by extraction, distillation, crystallization and column chromatography.

Solvates, such as hydrates, of reactants or products may be employed or prepared as appropriate in any of the methods of the present invention.

The abbreviations used herein are conventional abbreviations widely employed in the art. Some of which are:

| | |
|---|---|
| Ac | acetyl |
| AcOH | acetic acid |
| Bz | benzoyl |
| BOC | tert-butoxycarbonyl |
| BOC₂O | di-tert-butylcarbonate |
| CBZ | benzyloxycarbonyl |
| CBZ-Cl | benzyloxycarbonyl chloride |
| DCC | dicyclohexylcarbodiimide |
| DCU | N,N-dicyclohexylurea |
| DMAC | N,N-dimethylacetamide |
| DMAP | 4-dimethylaminopyridine |
| DMEU | N,N'-dimethylethyleneurea |
| DMF | dimethylformamide |
| DMPU | N,N'dimethylpropyleneurea |

-continued

| | |
|---|---|
| EtOAc | ethyl acetate |
| h | hour(s) |
| ipa | isopropyl alcohol |
| KHMDS | potassium hexamethyldisilazane |
| LiHMDS | lithium hexamethyldisilazine or lithium bis(trimethylsilyl)amide |
| LitbuO | lithium tert-butoxide |
| MeOH | methanol |
| min | minutes |
| MTBE | tert-butylmethyl ether |
| NaHMDS | sodium hexamethyldisilazane |
| NMPO | N-methyl-2-pyrrolidinone |
| Ph | phenyl |
| rt | room temperature |
| tBu | tertiary butyl |
| TBS | tributylsilyl |
| TES | triethylsilyl |
| THF | tetrahydrofuran |
| TFA | trifluoroacetic acid |
| TROC | 2,2,2-trichloromethoxycarbonyl |

EXAMPLES

The following Examples represent preferred embodiments of the invention. All temperatures are expressed in degrees Centigrade unless otherwise indicated.

Example 1

(8)

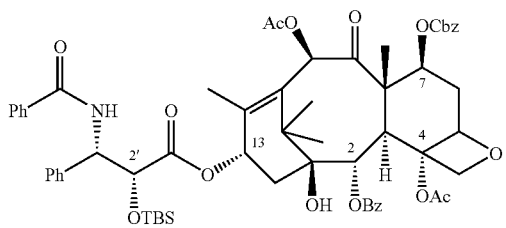

Paclitaxel (200.0, 234.2 mmol), imidazole (44.6 g, 654.9 mmol) and TBSCl (78.4 g, 520.2 mmol) were charged to a reaction vessel at 15–25° C. under $N_2$. The reaction vessel was cooled to 0° C. and 500 mL of DMF was added and the mixture was agitated for 10 hrs at 0–10° C. 2000 mL of EtOAc was added in 15 min. The reaction mixture was washed with 900 mL of DI water three times. The volume of rich EtOAc solution was reduced to 850 mL and cooled to 10–15° C. with agitation. CbzCl (76.2 mL, 533.7 mmol) was added in one portion and followed by t-BuOLi (693.2 mL, 10.5 wt % in heptane, 627.4 mmol) over 30 minutes while maintaining temperature of 10–20° C. The reaction mixture was agitated at 10–20° C. for 2 hrs to form the title compound. The reaction mixture was quenched and washed with 900 mL of DI water three times. The product rich organic solution was heated to 55–65° C. and 2280 mL heptane was added over 30 minutes while maintaining temperature of 55–65° C. The slurry was held at 55–65° C. for 1 h and cooled to 15–25° C. The product was vacuum filtered, the white wet cake was washed with two 700 mL portions of 1:6 v/v EtOAc:heptane. The cake was dried under vacuum (25–30 in Hg) at 55–60° C. to give 231.1 g of title compound (89.5 M %) with an HPLC purity of 99.1 AP.

$^1$H NMR 300 MHz: δ 8.20–7.25 (m, 20H); 7.1 (d, 1H); 6.45 (s, 1H); 6.3 (t, 1H); 5.85 (d, 1H); 5.70 (d, 1H); 5.55 (m, 1H); 5.20 (q, 2H); 5.05 (d, 1H); 470 (s, 1H); 4.40 (d, 1H); 4.25 (d, 1H); 4.05 (d, 1H); 2.70–2.55 (m, 1H); 2.65 (s, 3H); 2.50–2.40 (m, 1H); 2.20 (s, 3H); 2.05 (s, 3H); 1.85–1.75 (m, 6H); 1.20 (s, 3H); 1.15 (s, 3H); 0.85 (s, 9H); −0.05 (s, 3H); −0.35 (s, 3H). $^{13}$C NMR 75 MHz: δ 199.75, 169.58, 168.06, 167.11, 165.07, 165.02, 152.28, 139.16, 136.39, 133.40, 132.19, 131.86, 130.89, 129.94, 128.32, 127.12, 126.87, 126.72, 126.55, 126.48, 126.10, 125.12, 124.50, 82.05, 79.02, 76.82, 75.60, 75.38, 75.18, 74.75, 74.49, 73.52, 73.38, 73.20, 72.57, 68.26, 54.18, 53.81, 44.98, 41.45, 24.51, 23.65, 21.13, 18.91, 16.24, 12.80, 8.87.

Example 2

(9)

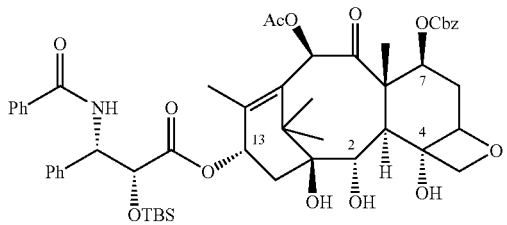

150 g of Example 1 compound (0.1361 mol, 1 equiv) was dissolved in 3.75 L of $CH_2Cl_2$. The solution was then cooled to −10° C. To this solution, 51.1 mL of BTMAM (benzyltrimethylammonium methoxide, 40 wt % in MeOH, 0.1021 mol, 0.75 equiv) was added while maintaining a reaction temperature of −10° C. The reaction mixture was then held at −10° C. until judged complete by HPLC (~4 hours). The reaction was then quenched with 7.81 mL of acetic acid (0.1361 mol) and held at −10° C. for 30 minutes. Next, the solvent was exchanged $CH_2Cl_2$ from to EtOAc under reduced pressure (final volume ~3.75 L). The EtOAc layer was then washed two times with 5 wt % $NaHCO_3$ (750 mL each, 5 mL/g '955), followed by two water washes (750 mL each) at 25° C. An azeotropic distillation to remove water was then completed under reduced pressure, and the solution was cooled to 25° C. (final volume ~3.75 L).

Example 3

(10)

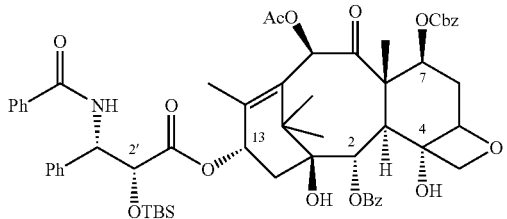

The solution from Example 2 was cooled to 0° C., and 15.8 mL of benzoyl chloride (0.1361 mol, 1.0 equiv, based on Example 1 compound, was added. Next, lithium t-butoxide (10 wt % in heptanes, 0.1497 mol, 1.1 equiv based on Example 1 compound was added, while maintaining the reaction temperature at 0±3° C. The reaction was held at 0° C. until judged complete by HPLC (15–30 minutes). The reaction mixture was then washed with 5 wt % $NaHCO_3$ two times (750 mL each, 5 mL/g 433955), at 25° C. Two water washes (750 mL each) were done next. A solvent exchange from EtOAc to EtOH (SDA 3A) was done at atmospheric pressure (final volume in EtOH ~1.2 L, or 8 mL/g Example 1 compound). To this EtOH solution at 40° C. was added 300 mL IPA. Crystallization of title compound occurred at ~40° C.; if crystallization does not occur the solution can be seeded. Upon crystallization, the slurry was held at 40° C. for 30 minutes, then heated to 50–55° C. for 1–2 hours. The slurry was then cooled to 0° C. and held for 2–4 hours. The slurry was then filtered, washed with EtOH (75 mL), and dried at ≦50° C. under reduced pressure to an LOD of <1.0%. The title product was isolated as an alcohol solvate. The resulting title compound was a white crystalline solid with ≧98 AP. Typical overall yield of the telescope procedure was 58–60%, based on the Example 1 charge.

$^1$H NMR 300 MHz: δ −0.27 (s, 3H), −0.11 (s, 3H), 0.82 (s, 9H), 1.10 (s, 3H), 1.71 (br s, 4H), 1.95–2.14 (m, 1H), 2.14 (s, 3H), 2.16 (s, 3H), 2.21 (s, 3H), 2.27–2.38 (m, 1H), 2.52–2.65 (m, 1H), 2.8 (dd, 1H, J=6.0, 15.0 Hz), 3.55 (d, 1H, J=3.0 Hz), 4.16 (d, 1H, J=9.0 Hz), 4.27 (d, 1H, J=9.0 Hz), 4.55 (s, 1H), 4.88 (s, 1H), 4.93–4.97 (dd, 1H, J=6.0, 12.0 Hz), 5.15–5.29 (m, 3H), 5.7 (d, 1H, J=6.0 Hz), 5.90–5.98 (m, 1H), 6.09–6.12 (dd, 1H, J=3.0, 9.0 Hz), 6.46 (s, 1H), 7.20–7.56 (m, 16H), 7.79 (d, 2H, J=6.0 Hz), 8.19 (d, 2H, J=6.0 Hz).

13C NMR 300 MHz: δ 09.60, 15.64, 17.34, 17.41, 17.90, 19.93, 24.34, 24.58, 26.65, 30.00, 41.93, 54.15, 55.30, 57.42, 69.36, 70.43, 73.44, 75.26, 75.66, 76.08, 76.22, 76.29, 76.51, 125.80, 126.10, 126.99, 127.54, 127.64, 127.76, 127.92, 129.43, 130.92, 132.57, 133.73, 134.20, 134.27, 138.11, 138.71, 153.58, 166.16, 166.85, 168.28, 169.29, 201.18.

Example 4

(11)

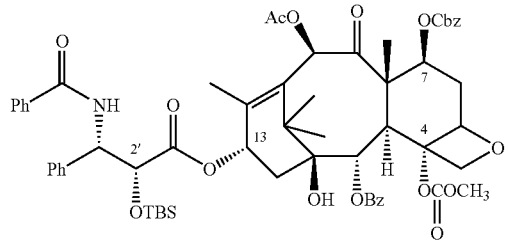

150 g of Example 3 ethanol solvate (0.1356 mol, 1 equiv) was dissolved in 4.5 L of ethyl acetate. Three liters of ethyl acetate were distilled off at atmospheric pressure. 79 mL (5 volume %) of anhydrous DMF was added, and the reaction mixture was cooled to −15° C. Methyl chloroformate was added (14.2 mL, 1.3 equiv), followed by lithium tert butoxide (10 wt % in heptane, 361 mL, 2.2 eq) at a rate to keep the reaction temperature below −10° C. (15 min). After stirring at <−10° C. for one hour, the reaction was quenched by the addition of 1 M $H_3PO_4$ (750 mL). The aqueous layer was drained off, and the rich organic layer was washed with 1500 mL of water. The aqueous layer was again removed, and the rich organic layer was reduced in volume to 750 mL by atmospheric distillation. The temperature was maintained at >50° C., and 2250 mL of heptane was added over 1 hour. The white slurry was cooled to rt and vacuum filtered. The white recipitate was washed with IL of heptane, then dried at 50° C. in a vacuum oven for 24 hours. The desired title compound was obtained in 91% yield (137 g) and 99.3 HPLC purity.

$^1$H NMR 400 MHz: δ 8.20–7.25 (m, 20H); 7.1 (d, 1H); 6.45 (s, 1H); 6.3 (t, 1H); 5.85 (d, 1H); 5.70 (d, 1H); 5.55 (m, 1H); 5.20 (q, 2H); 5.05 (d, 1H); 470 (s, 1H); 4.40 (d, 1H); 4.25 (d, 1H); 4.05 (d, 1H); 4.00 (s, 3H); 2.70–2.55 (m, 1H); 2.50–2.40 (m, 1H); 2.20 (s, 3H); 2.05 (s, 3H); 1.85–1.75 (m, 6H); 1.20 (s, 3H); 1.15 (s, 3H); 0.85 (s, 9H); −0.05 (s, 3H); −0.35 (s, 3H). $^{13}$C NMR 100 MHz: δ 200.71, 171.05, 168.50, 166.46, 153.80, 152.18, 140.93, 138.50, 135.05, 134.10, 133.58, 132.75, 131.57, 129.99, 128.90, 128.62, 128.45, 128.28, 127.67, 126.85, 126.34, 83.84, 83.14, 78.72, 76.17, 75.60, 75.45, 74.68, 71.11, 70.52, 56.89, 56.34, 55.90, 47.76, 43.77, 36.24, 33.89, 27.08, 26.19, 21.81, 21.48, 18.88, 15.65, 11.60, −4.28, −4.90.

Example 5

(2)

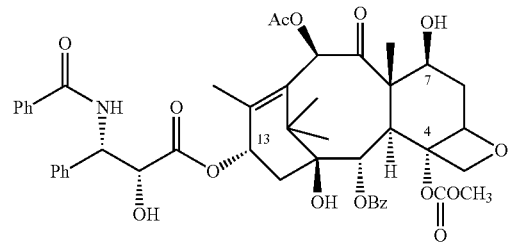

150 g of Example 4 compound (0.13417 mol, 1 equiv) was dissolved in 1.5 L of ethyl acetate. To the above solution was added 9.21 mL glacial HOAc (0.16088 mol, 1.2 equiv) at ambient temperature. 1.0 M Tetrabutylammonium fluoride in THF (0.161 mol, 1.2 equiv) was charged to the reaction mixture. After stirring at ambient temperature for 30 min, the starting material, Example 4 compound, was completely consumed. To the above reaction mixture was charged a slurry of 11.4 g 5% Pd/C (0.00268 mol, 0.02 equiv) in EtOAc under nitrogen. 42.3 g Ammonium formate (0.67079 mol, 5 equiv) was then added. The reaction mixture was heated to 50° C. for 40 min to completely convert to title compound. The reaction mixture was passed through a short bed of Hyflo. The organic phase was washed with 876 mL DI water three times until no fluoride ion remained. A solvent swap from EtOAc to absolute EtOH (200 proof) was carried out under azeotropic distillation. The final EtOH organic solution was reduced in volume to 450 mL. The temperature was maintained at 65–70° C., and 1250 mL of heptane was added to the above solution. The slurry was held at 60° C. for 2 h, and cooled to rt and vacuum filtered. The white cake was washed with 150 mL of heptane/EtOH (v/v~4/1), then dried at 55–65° C. in a vacuum oven for 24 hours. The desired title compound was obtained in 87% yield (101.4 g) and 99.13 HPLC purity.

$^1$H NMR 300 MHz: δ 1.14 (s, 3H), 1.22 (s, 3H), 1.68 (s, 3H), 1.84 (s, 3H), 1.89 (m, 1H), 2.00 (S, 1H), 2.24 (s, 3H), 2.30 (dd, 1H, J=9.0, 18.0 Hz), 2.44 (dd, 1H, J=9.0, 15.0 Hz), 2.52 (m, 1H), 3.68 (d, 1H, J=3.0 Hz), 3.82 (s, 3H), 3.86 (d, 1H, J=9.0 Hz), 4.22 (d, 1H, J=9.0 Hz), 4.35 (d, 1H, J=6.0 Hz), 4.38 (m, 1H), 4.80 (dd, 1H, J=3.0, 6.0 Hz), 4.97 (dd, 1H, J=3.0, 12.0 Hz), 5.71 (d, 1H, J=6.0 Hz), 5.83 (dd, 1H, J=3.0, 12.0 Hz), 6.20 (t, 1H, J=9.0 Hz), 6.27 (s, 1H), 6.98 (d, 1H, J=9.0 Hz), 7.32–7.63 (m, 11H), 7.73 (d, 2H, J=9.0 Hz), 8.15 (d, 2H, J=9.0 Hz). $^{13}$C NMR 75 MHz: δ 9.64, 14.96, 20.87, 21.72, 26.86, 35.40, 35.82, 43.08, 45.88, 54.76, 56.02, 58.31, 71.98, 72.24, 73.03, 74.87, 75.59, 75.99, 78.84, 83.13, 84.09, 127.04, 127.11, 128.27, 128.69, 128.74, 128.96, 129.12, 130.224, 131.92, 133.36, 133.74, 138.43, 142.09, 153.13, 166.95, 167.04, 171.33, 172.96, 203.50.

What is claimed is:

1. A compound having the structure

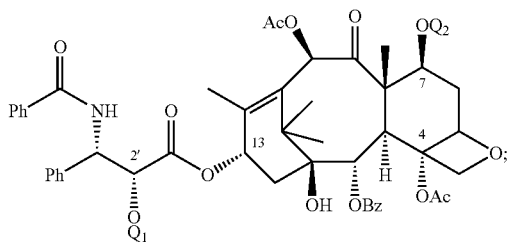

(8)

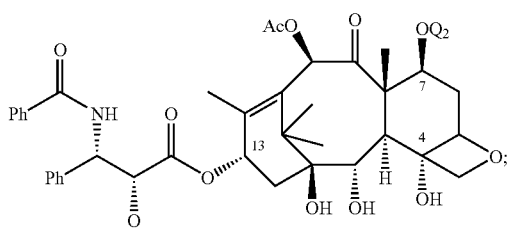

(9)

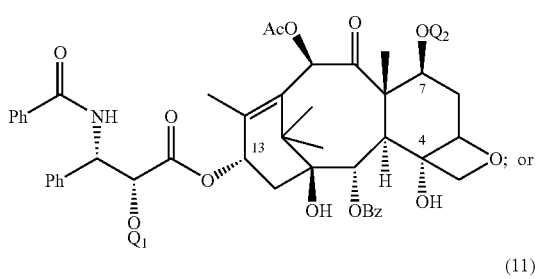

(10)

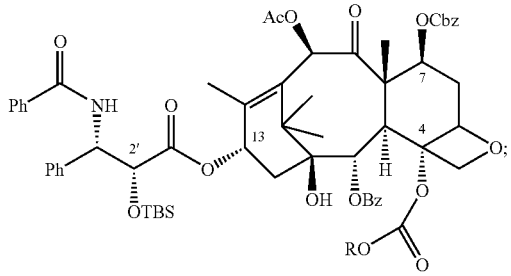

(11)

wherein $Q_1$ is tri $C_1-C_4$ alkylsilyl;

$Q_2$ is an electrophilic protecting group selected from the group consisting of benzoyloxycarbonyl (Cbz), t-butoxycarbonyl (BOC), and those provided by an electrophilic protecting agent of the general formula

wherein $R^x$ is alkyl, aryl, R'O—, R'$_2$N—, or R'S, and X is halogen, imidazoyl, benzotriazole, N-(benzyloxycarboxyloxy) succinimide, OR', or —OOCOR' and wherein R' is alkyl or alkenyl having 1–6 carbons atoms, benzyl, phenyl, trichloroethyl, trifluoroethyl, 2-trimethylsilylethyl or triisopropylsilyl; and R is $C_1-C_7$ alkyl or aryl, and all stereoisomers thereof.

2. The compound as defined in claim 1 wherein $Q_1$ is tert-butyldimethylsilyl.

3. The compound as defined in claim 1 wherein R is alkyl.

4. The compound as defined in claim 3 wherein R is methyl.

5. The compound as defined in claim 1 wherein $Q_2$ is benzoyloxycarbonyl.

6. A process for preparing compound (9) as defined in claim 1 having the structure

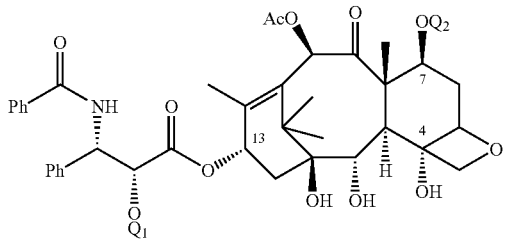

(9)

where $Q_1$ is tri $C_1-C_4$ alkylsilyl, and $Q_2$ is an electrophilic protecting group selected from the group consisting of benzoyloxycarbonyl (Cbz), t-butoxycarbonyl (BOC), and those provided by an electrophilic protecting agent of the general formula

wherein $R^x$ is alkyl, aryl, R'O—, R'$_2$N—, or R'S, and X is halogen, imidazoyl, benzotriazole, N-(benzyloxycarboxyloxy) succinimide, OR', or —OOCOR' and wherein R' is alkyl or alkenyl having 1–6 carbons atoms, benzyl, phenyl, trichloroethyl, trifluoroethyl, 2-trimethylsilylethyl or triisopropylsilyl, which comprises:

(a) subjecting paclitaxel having the structure

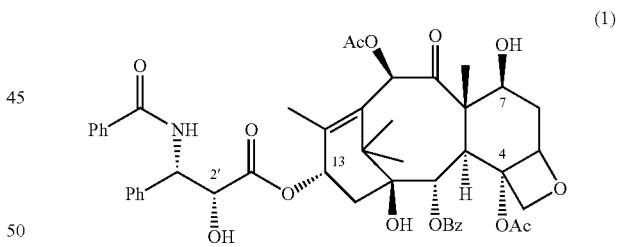

(1)

to silyl protection by treating paclitaxel with a tri $C_1-C_4$ alkylsilyl chloride in the presence of a base and organic solvent to form the protected compound (7) of the structure

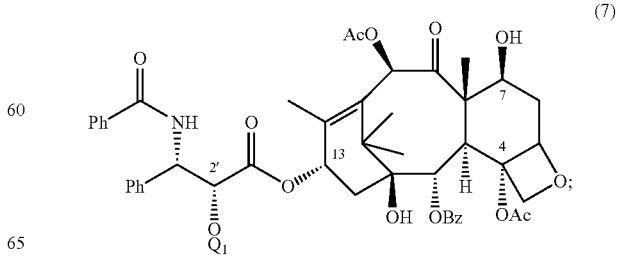

(7)

(b) treating compound (7) with a $Q_2$ protecting agent to provide a $Q_2$ protecting group as defined above in the presence of a base and an organic solvent to form the $Q_2$ protected compound (8) of the structure

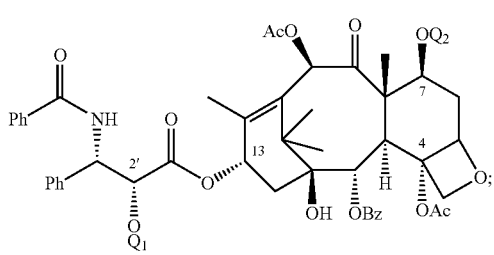

(8)

and (c) deprotecting compound (8) by treating compound (8) with an ammonium compound of the structure $$(R_x)_4N^+X$$

wherein $R_x$ is $C_1$–$C_7$ alkyl or aryl, and X is $OCH_3$ or a halogen, in the presence of dichloromethane to form compound (9).

7. The process as defined in claim 6 wherein $Q_1$ is tert-butyldimethylsilyl; and $Q_2$ is benzoyloxycarbonyl, and wherein the base in step (a) is imidazole, pyridine, or a tertiary amine, and the organic solvent has the structure $$R^1C\overset{O}{\|}{-}OR^2$$

wherein $R^1$ and $R^2$ are the same or different and are $C_1$–$C_4$ alkyl;

wherein the base in step (b) has the structure $$R^3OM$$

wherein $R^3$ is $C_1$–$C_6$ alkyl and M is Li, Na or K, and the organic solvent is an ester or amide organic solvent, and the Cbz protecting agent has the structure $CbzX_1$ wherein $X_1$ is Cl, Br or F, and wherein the ammonium compound used in step (c) is benzyltrimethylammonium chloride, tetrabutylammonium chloride or benzyltrimethylammonium methoxide.

8. The process as defined in claim 7 wherein in step (a) the base is imidazole, pyridine, triethylamine (TEA), or diisopropylethylamine (DIPEA), and the organic solvent is dimethyl formamide (DMF), N,N'-dimethylacetamide (DMAC), N,N'-dimethylpropyleneurea (DMPU), N,N'-dimethylethyleneurea (DMEU) or N-methyl-2-pyrrolidone (NMPO);

wherein in step (b) the base is Li t-butoxide and the organic solvent is methyl acetate, ethyl acetate, butyl acetate, dimethyl formamide (DMF), N,N'-dimethylacetamide (DMAC), N,N'-dimethylpropyleneurea (DMPU), N,N'-dimethylethyleneurea (DMEU) or N-methyl-2-pyrrolidone (NMPO); and wherein in step (c) the ammonium compound is benzyltrimethylammonium methoxide and step (c) is carried out at a temperature of below about $-10°$ C.

9. The process as defined in claim 6 wherein in step (a) the paclitaxel is treated with tert-butyldimethylsilyl chloride in the presence of imidazole and dimethylformamide;

wherein in step (b) compound (7) is treated with CbzCl in the presence of Li t-butoxide and ethyl acetate; and wherein in step (c) compound (8) is treated with benzyltrimethylammonium methoxide in the presence of dichloromethane at a temperature within the range from about $-10°$ to about $-20°$ C.

10. A process for preparing a compound of the structure (2)

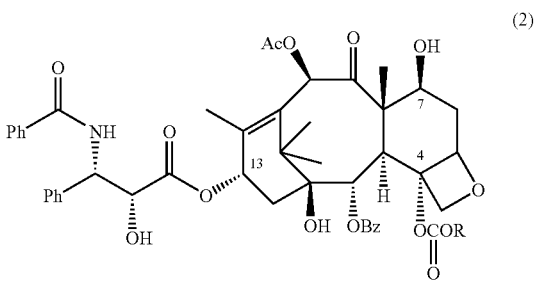

wherein R is $C_1$–$C_7$ alkyl or aryl, which comprises:

(a) providing a Cbz protected compound of the structure (9)

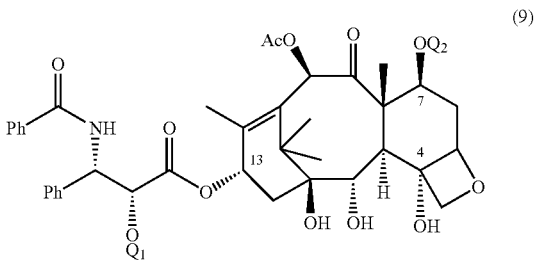

where $O_2$ is Cbz, as defined in claim 1;

(b) treating compound (9) with a benzoyl (Bz) protecting agent in the presence of a base and an organic solvent to form the Bz protected compound (10),

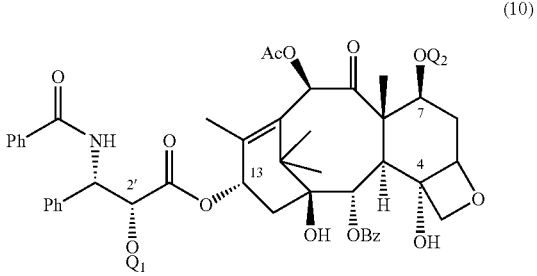

(c) subjecting compound (10) to carbonate formation by treating compound (10) with a haloformate of the structure ROOCX wherein X is Cl, Br, F or I, $(ROOC)_2O$, or R-pyrocarbonate, wherein R is $C_1$–$C_7$ alkyl or aryl, in the presence of an organic solvent, a base and a catalyst to form R-oxycarbonyl substituted compound (11) of the structure (11)

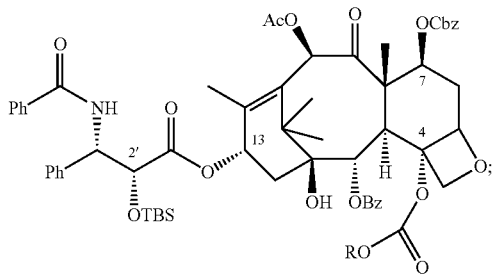

and (d) subjecting compound (11) to catalytic transfer-hydrogenation by treating compound (11) with a deprotecting agent in the presence of an organic acid, organic solvent, catalyst and formate compound or hydrogen, to form the compound (2).

11. The process as defined in claim 10 wherein in step (b) the benzoyl protecting agent is benzoyl chloride, benzoyl bromide, benzoyl fluoride or benzoyl anhydride $(Bz)_2O$; the base in step (b) has the structure $R^3OM$ wherein $R^3$ is $C_1$–$C_6$ alkyl and M is Li, Na or K, and the organic solvent is an ester or amide organic solvent;

wherein in step (c) the haloformate is methylchloroformate, the base is $R^{3'}OM'$ wherein $R^{3'}$ is $C_1$–$C_6$ alkyl and M' is Li, Na or K, the organic solvent is an ester or amide organic solvent, and the catalyst is dimethylformamide, 1,3-dimethyl-3,4,5,6-tetrahydro-2(1H)-pyrimidinone (DPMU), 1,3-dimethyl-2-imidazolidinone (DMEU) or N-methyl-2-pyrrolidinone (NMPO), and wherein the alkyl or aryl formate is $CH_3OOCCl$;

wherein in step (d) the deprotecting agent is tetrabutylammonium fluoride, hydrogen fluoride, triethylamineb 3HF or M"F where M" is Na, Li or K, the acid is $C_1$–$C_4$ alkyl COOH, the organic solvent is an ester or amide organic solvent, and the catalyst is palladium, platinum or ruthenium, and the formate compound is ammonium formate, sodium formate, or formic acid.

12. The process as defined in claim 10 wherein in step (b) the benzoyl protecting agent is benzoyl chloride, the base is Li t-butoxide, and the organic solvent is ethyl acetate;

wherein in step (c) the base is Li t-butoxide, the haloformate is methyl chloroformate, the organic solvent is ethyl acetate and the catalyst is dimethyl formamide; and wherein in step (d) the deprotecting agent is tetrabutylammonium fluoride, the acid is acetic acid, the organic solvent is ethyl acetate, the catalyst is Pd/C and the formate compound is ammonium formate.

13. A process for preparing a taxane having the structure (2)

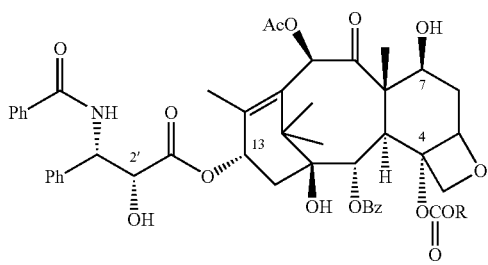
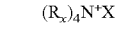

wherein R is $C_1$–$C_7$ alkyl or aryl, which comprises:

(a) subjecting paclitaxel having the structure (1)

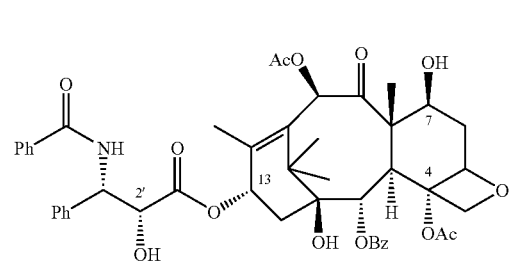

to silyl protection by treating paclitaxel with a tri-$C_1$–$C_4$-alkylsilylchloride in the presence of a base and organic solvent to form the protected compound (7) of the structure (7)

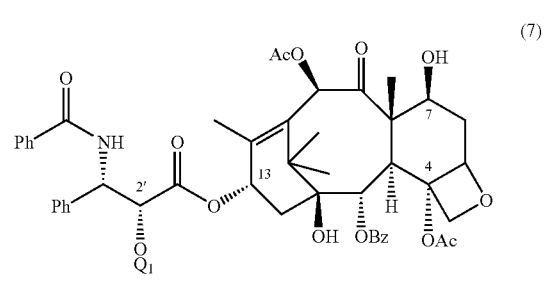

wherein $Q_1$ is a tri $C_1$–$C_4$ alkylsilyl group;

(b) treating compound (7) with an electrophilic protecting agent to provide a $Q_2$ electrophilic protecting group selected from the group consisting of benzoyloxycarbonyl (Cbz), t-butoxycarbonyl (BOC), and those of the general formula

wherein $R^x$ is alkyl, aryl, R'O—, $R'_2N$—, or R'S, wherein R' is alkyl or alkenyl having 1–6 carbons atoms, benzyl, phenyl, trichloroethyl, trifluoroethyl, 2-trimethylsilylethyl or triisopropylsilyl; which is in the presence of a base and an organic solvent to form the 7-protected compound (8) of the structure (8)

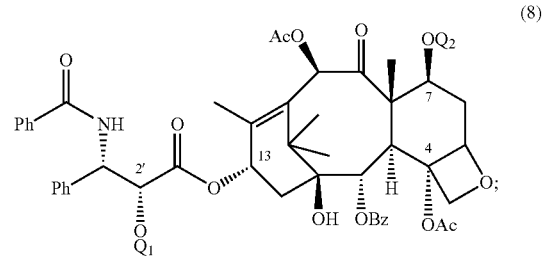

(c) deprotecting compound (8) by treating compound (8) with an ammonium compound of the structure $(R_x)_4N^+X$ wherein $R_x$ is $C_1$–$C_7$ alkyl or aryl, and X is $OCH_3$ or a halogen, in the presence of dichloromethane to form compound (9);

(d) treating compound (9) with a benzoyl (Bz) protecting agent in the presence of a base and an organic solvent to form the Bz protected compound (10),

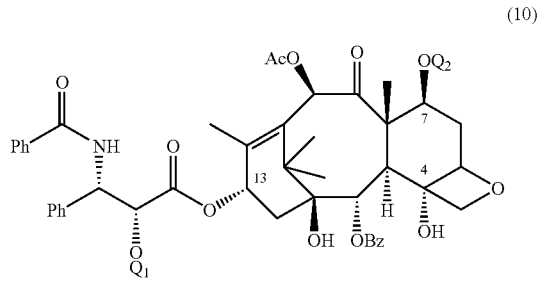

(10)

(e) subjecting compound (10) to carbonate formation by treating compound (10) with a haloformate of the structure ROOCX wherein X is Cl, Br, F or I, $(ROOC)_2O$, or R-pyrocarbonate, in the presence of an organic solvent, a base and a catalyst to form R-oxycarbonyl substituted compound (11) of the structure

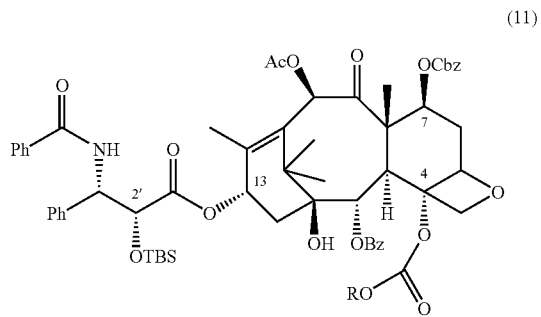

(11)

and (f) subjecting compound (11) to catalytic transfer-hydrogenation by treating compound (11) with a deprotecting agent in the presence of an organic acid, organic solvent, catalyst and formate compound or hydrogen, to form the compound (2).

14. The process as defined in claim 13 wherein the tri $C_1$–$C_4$ alkylsilyl chloride is tert-butyldimethylsilyl chloride; the base in step (a) is imidazole, pyridine, or tertiary amine and the organic solvent has the structure $$R^1C(=O)-OR^2$$

wherein $R^1$ and $R^2$ are the same or different and are $C_1$–$C_4$ alkyl;

wherein the base in step (b) has the structure $R^3OM$ wherein $R^3$ is $C_1$–$C_6$ alkyl, and M is Li, Na or K, and the organic solvent is an ester or amide organic solvent, and the Cbz protecting agent has the structure $CbzX_1$ wherein $X_1$ is Cl, Br or F; and wherein the ammonium compound used in step (c) is benzyltrimethylammonium chloride, tetrabutylammonium chloride or benzyltrimethylammonium methoxide;

wherein in step (d) the benzoyl protecting agent is benzoyl chloride, benzoyl bromide, benzoyl fluoride or benzoyl anhydride $(Bz)_2O$;

the base in step (d) has the structure $R^3OM$ wherein $R^3$ is $C_1$–$C_6$ alkyl and M is Li, Na or K, and the organic solvent is an ester or amide organic solvent;

wherein in step (e) the haloformate is methylchloroformate, the base is $R^{3'}OM'$ wherein $R^{3'}$ is $C_1$–$C_6$ alkyl and M' is Li, Na or K, the organic solvent is an ester or amide organic solvent, and the catalyst is dimethylformamide, 1,3-dimethyl-3,4,5,6-tetrahydro-2(1H)-pyrimidinone (DPMU), 1,3-dimethyl-2-imidazolidinone (DMEU) or N-methyl-2-pyrrolidinone (NMPO), and wherein the alkyl or aryl formate is $CH_3OOCCl$;

wherein in step (f) the deprotecting agent is tetrabutylammonium fluoride, hydrogen fluoride, triethylamine 3HF or M"F where M" is Na, Li or K, the acid is $C_1$–$C_4$ alkyl COOH, the organic solvent is an ester or amide organic solvent, and the catalyst is palladium, platinum or ruthenium, and the formate compound is ammonium formate, sodium formate, or formic acid.

15. The process as defined in claim 14 wherein in step (a) the base is imidazole, pyridine, triethylamine (TEA), or diisopropylethylamine (DIPEA), and the organic solvent is dimethyl formamide (DMF), N,N'-dimethylacetamide (DMAC), N,N'-dimethylpropyleneurea (DMPU), N,N'-dimethylethyleneurea (DMEU) or N-methyl-2-pyrrolidone (NMPO); wherein in step (b) the base is Li t-butoxide and the organic solvent is methyl acetate, ethyl acetate, butyl acetate, dimethyl formamide (DMF), N,N'-dimethylacetamide (DMAC), N,N'-dimethylpropyleneurea (DMPU), N,N'-dimethylethyleneurea (DMEU) or N-methyl-2-pyrrolidone (NMPO); and wherein in step (c) the ammonium compound is benzyltrimethylammonium methoxide and step (c) is carried out at a temperature of below about $-10°$ C.;

wherein in step (d) the benzoyl protecting agent is benzoyl chloride, the base is Li t-butoxide, and the organic solvent is ethyl acetate;

wherein in step (e) the base is Li t-butoxide, the haloformate is methyl chloroformate, the organic solvent is ethyl acetate and the catalyst is dimethyl formamide; and wherein in step (f) the deprotecting agent is tetrabutylammonium fluoride, the acid is acetic acid, the organic solvent is ethyl acetate, the catalyst is Pd/C and the formate compound is ammonium formate.

16. The process as defined in claim 15 wherein in step (a) the paclitaxel is treated with tert-butyldimethylsilyl chloride in the presence of imidazole and dimethylformamide, wherein in step (b) compound (7) is treated with CbzCl in the presence of Li t-butoxide and ethyl acetate; and wherein in step (c) compound (8) is treated with benzyltrimethylammonium methoxide in the presence to dichloromethane at a temperature within the range from about $-10°$ to about $-20°$ C.

* * * * *